(12) United States Patent
Suh et al.

(10) Patent No.: US 12,324,923 B2
(45) Date of Patent: Jun. 10, 2025

(54) IMPLANT SYSTEM INCLUDING WAKE-UP DEVICE AND OPERATING METHOD OF IMPLANT SYSTEM INCLUDING WAKE-UP DEVICE

(71) Applicant: Samsung Electronics Co., Ltd., Suwon-si (KR)

(72) Inventors: Junyeub Suh, Suwon-si (KR); Sang Joon Kim, Hwaseong-si (KR); Hankyu Lee, Suwon-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 0 days.

(21) Appl. No.: 18/181,040

(22) Filed: Mar. 9, 2023

(65) Prior Publication Data

US 2023/0201611 A1   Jun. 29, 2023

Related U.S. Application Data

(63) Continuation of application No. 16/857,416, filed on Apr. 24, 2020, now Pat. No. 11,623,101.

(30) Foreign Application Priority Data

Nov. 26, 2019   (KR) .................. 10-2019-0153647

(51) Int. Cl.
*A61N 1/378*   (2006.01)
*A61N 1/36*   (2006.01)
*A61N 1/37*   (2006.01)

(52) U.S. Cl.
CPC .......... *A61N 1/378* (2013.01); *A61N 1/3787* (2013.01); *A61N 1/36128* (2013.01); *A61N 1/3708* (2013.01)

(58) Field of Classification Search
CPC .. A61N 1/3708; A61N 1/37276; A61N 1/378; A61N 1/36142
See application file for complete search history.

(56) References Cited

U.S. PATENT DOCUMENTS 5,342,408 A * 8/1994 deCoriolis ......... A61N 1/37276
                                                                607/32
2006/0031692 A1   2/2006 Kato et al.
(Continued)

FOREIGN PATENT DOCUMENTS

| KR | 98-11219 A | 4/1998 |
| KR | 10-2009-0065086 A | 6/2009 |
| KR | 10-1550348 B1 | 9/2015 |

OTHER PUBLICATIONS

Signoretta, Emanuele., "Insight Into ESP32 Sleep Modes & Their Power Consumption", *Open Electronics*, Jan. 25, 2020 (7 pages in English).

(Continued)

*Primary Examiner* — George R Evanisko
(74) *Attorney, Agent, or Firm* — NSIP Law

(57) ABSTRACT

An implant system includes an implant device configured to generate a stimulation signal for a user using a power manager according to an operation mode based on biometric information of the user, and a wake-up device configured to switch the operation mode based on either one or both of an energy supply received through an external energy source different from the power manager and a result of counting a timer.

3 Claims, 5 Drawing Sheets

(56) References Cited

U.S. PATENT DOCUMENTS

2007/0250126 A1* 10/2007 Maile .................. A61N 1/3706
 607/16
2008/0155289 A1 6/2008 Fernald et al.
2015/0065047 A1 3/2015 Wu et al.
2016/0098076 A1 4/2016 Chng et al.

OTHER PUBLICATIONS

Korean Office Action Issued on Nov. 26, 2024, in Counterpart Korean Patent Application No. 10-2019-0153647 (3 Pages in English, 7 Pages in Korean).

* cited by examiner

P: Power management turn on power
t: Sleep time
S: Sleep mode power consumption
D: Deep sleep mode power consumption

IMPLANT SYSTEM INCLUDING WAKE-UP DEVICE AND OPERATING METHOD OF IMPLANT SYSTEM INCLUDING WAKE-UP DEVICE

CROSS-REFERENCE TO RELATED APPLICATIONS

This application is a continuation of application Ser. No. 16/857,416 filed on Apr. 24, 2020 which claims the benefit under 35 USC § 119(a) of Korean Patent Application No. 10-2019-0153647 filed on Nov. 26, 2019 in the Korean Intellectual Property Office, the entire disclosures of which are incorporated herein by reference for all purposes.

BACKGROUND

1. Field

The following description relates to an implant system including a wake-up device. The following description also relates to an operating method of an implant system including a wake-up device.

2. Description of Related Art

In general, an implant device to be implanted into a body of a user may include a stimulating function and a partial sensing function for treatment on an extremely limited volume, for example, 1 cc to 30 cc, and may support a wireless communication function to communicate with an external device for simple control. Once the implant device is implanted into a body, the implant device may aim to guarantee its successful operation for a considerable period, for example, several months to several years, for convenient use. Thus, various methods for reducing power consumption may be under consideration.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, an implant system includes an implant device configured to generate a stimulation signal for a user using a power manager according to an operation mode based on biometric information of the user, and a wake-up device configured to switch the operation mode based on either one or both of an energy supply received through an external energy source different from the power manager and a result of counting a timer.

The wake-up device may include a real-time clock (RTC) connected directly to a battery of the implant device and configured to count the timer for operation mode switching between a power saving mode and an active mode, and a wireless power transfer device configured to switch the operation mode based on whether energy is supplied by the external energy source separate from the battery.

The operation mode may include a power saving mode in which the implant device is in a sleep state, and an active mode in which the implant device is in an operating state, wherein the power saving mode may include a deep sleep mode in which the implant device including the power manager is in a sleep state, and a sleep mode in which the implant device except for the power manager is in a sleep state.

The implant device may include one or more processors configured to determine the operation mode to be the deep sleep mode or the sleep mode based on a power consumption according to a sleep duration of the implant device.

The one or more processors may be configured to determine the operation mode to be the deep sleep mode or the sleep mode based on a result of comparing a first power consumption to a second power consumption according to the sleep duration in the sleep mode, the first power consumption corresponding to a sum of a power consumption for booting the power manager from the deep sleep mode and a power consumption according to the sleep duration in the deep sleep mode.

The one or more processors may be configured to turn off an enable signal of the power manager at the same time as starting the counting of a timer value based on the sleep duration, in response to the operation mode being determined to be the deep sleep mode.

The one or more processors may be configured to store biometric information required for each application field of the implant system, in response to the operation mode being determined to be the deep sleep mode.

The wake-up device may be configured to turn on an enable signal of the power manager for the implant device to operate in the active mode based on whether a count value of the timer has expired.

The wake-up device may be configured to turn on an enable signal of the power manager, in response to a wireless energy supply being received through the external energy source.

The wake-up device may be configured to turn on the enable signal of the power manager based on an energy reception degree according to the wireless energy supply.

In another general aspect, a wake-up device for an implant device includes a real-time clock (RTC) connected directly to a battery of the implant device including a power manager and configured to count a timer for switching an operation mode of the implant device to a power saving mode or an active mode, and a wireless power transfer device configured to switch the operation mode based on an energy supply provided by an external energy source separate from the battery.

The RTC may be configured to turn on an enable signal of the power manager for the implant device to operate in the active mode based on whether a count value of the timer has expired.

The wireless power transfer device may be configured to turn on an enable signal of the power manager, in response to whether wireless energy is supplied through the external energy source, irrespective of whether a count value of the timer has expired.

The wireless power transfer device may be configured to turn on the enable signal of the power manager based on an energy reception degree according to the wireless energy supply.

In another general aspect, an operating method of an implant system includes sensing biometric information of a user, generating a stimulation signal for the user using a power manager according to an operation mode based on the biometric information, and switching the operation mode based on either one or both of an energy supply through an external energy source different from the power manager and a count value of a timer.

The switching may include counting the timer for operation mode switching between a power saving mode and an active mode, sensing either one or both of whether the timer has expired and whether energy is supplied by the external energy source, and switching the operation mode from the power saving mode to the active mode, in response to whether the timer has expired, or the energy being supplied to the external energy source being sensed before the timer has expired.

The operation mode may include the power saving mode in which the implant device is in a sleep state, and the active mode in which the implant device is in an operating state, wherein the power saving mode may include a deep sleep mode in which the implant device including the power manager is in a sleep state, and a sleep mode in which the implant device except for the power manager is in a sleep state.

The switching may include calculating a power consumption for booting the power manager and a power consumption for each power saving mode according to a sleep duration of the implant device, determining the operation mode to be one of the deep sleep mode or the sleep mode based on the calculated power consumptions, and switching the operation mode to the determined mode.

The operating method may further include in response to the operation mode being determined to be the deep sleep mode, turning off an enable signal of the power manager at the same time as starting counting of the timer based on the sleep duration, and storing biometric information required for each application field of the implant system.

In another general aspect, an operating method of a wake-up device includes setting a timer value of a real-time clock (RTC) connected directly to a battery and configured to provide a clock, based on a sleep duration of an implant device, turning off an enable signal of a power manager for the implant device including the power manager to operate in a power saving mode, in response to the RTC starting a counting according to the timer value, and turning on the enable signal of the power manager for the implant device to be activated based on whether the timer value has expired or whether energy is supplied through an external energy source different from the power manager.

In another general aspect, a non-transitory computer-readable storage medium stores instructions that, when executed by one or more processors, cause the one or more processors to perform the method described above.

In another general aspect, an implant system includes an implant device configured to generate a stimulation signal for a user according to an operation mode, wherein the operation mode includes a power saving mode in which the implant device is in a sleep state, and an active mode in which the implant device is in an operating state, and a wake-up device configured to switch the operation mode based on either one or both of an energy supply received through an external energy source different from a power manager used to generate the stimulation signal and a result of counting a timer.

The power saving mode may include a deep sleep mode in which the implant device including the power manager is in a sleep state, and a sleep mode in which the implant device except for the power manager is in a sleep state.

The implant device may include one or more processors configured to determine the operation mode to be the deep sleep mode or the sleep mode based on a power consumption according to a sleep duration of the implant device.

The wake-up device may be configured to turn on an enable signal of the power manager for the implant device to operate in the active mode based on whether a count value of the timer expired.

The wake-up device may be configured to turn on an enable signal of the power manager, in response to a wireless energy supply being received through the external energy source.

Other features and aspects will be apparent from the following detailed description, the drawings, and the claims.

Figure 1:
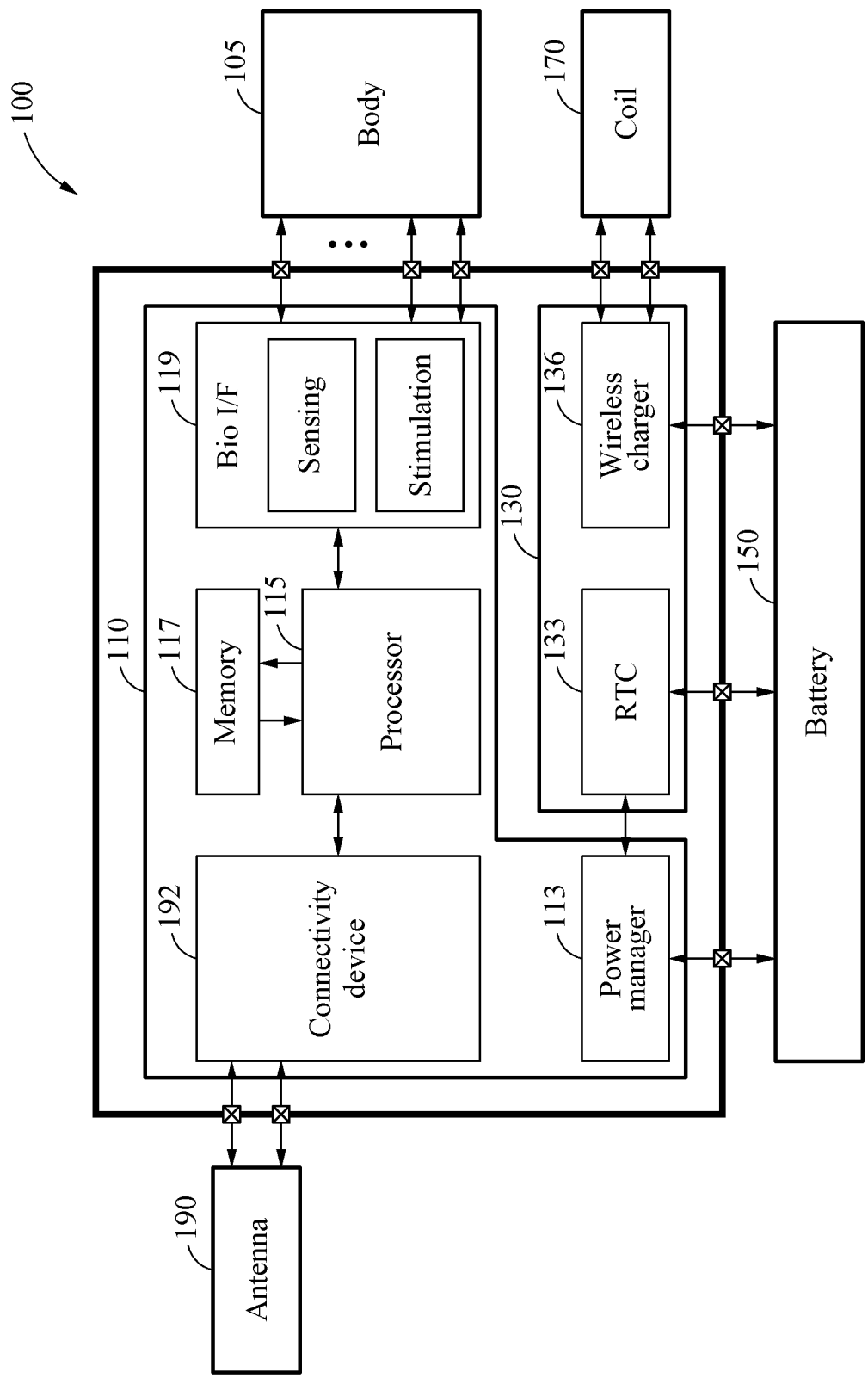
FIG. 1 illustrates an example of a configuration of an implant system.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween.

As used herein, the term "and/or" includes any one and any combination of any two or more of the associated listed items.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

Spatially relative terms such as "above," "upper," "below," and "lower" may be used herein for ease of description to describe one element's relationship to another element as shown in the figures. Such spatially relative terms are intended to encompass different orientations of the device in use or operation in addition to the orientation depicted in the figures. For example, if the device in the figures is turned over, an element described as being "above" or "upper" relative to another element will then be "below" or "lower" relative to the other element. Thus, the term "above" encompasses both the above and below orientations depending on the spatial orientation of the device. The device may also be oriented in other ways (for example, rotated 90 degrees or at other orientations), and the spatially relative terms used herein are to be interpreted accordingly.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Due to manufacturing techniques and/or tolerances, variations of the shapes shown in the drawings may occur. Thus, the examples described herein are not limited to the specific shapes shown in the drawings, but include changes in shape that occur during manufacturing.

The features of the examples described herein may be combined in various ways as will be apparent after an understanding of the disclosure of this application. Further, although the examples described herein have a variety of configurations, other configurations are possible as will be apparent after an understanding of the disclosure of this application.

Hereinafter, example embodiments will be described in detail with reference to the accompanying drawings. The scope of the right, however, should not be construed as limited to the example embodiments set forth herein. Like reference numerals in the drawings refer to like elements throughout the present disclosure.

Various modifications may be made to the example embodiments. Here, the examples are not construed as limited to the disclosure and should be understood to include all changes, equivalents, and replacements within the idea and the technical scope of the disclosure.

Unless otherwise defined, all terms including technical and scientific terms used herein have the same meaning as commonly understood by one of ordinary skill in the art to which examples belong, after an understanding of the present disclosure. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

Herein, it is noted that use of the term "may" with respect to an example or embodiment, e.g., as to what an example or embodiment may include or implement, means that at least one example or embodiment exists where such a feature is included or implemented while all examples and embodiments are not limited thereto.

FIG. 1 illustrates an example of a configuration of an implant system. Referring to the example of FIG. 1, an implant system 100 may include an implant device 110 and a wake-up device 130. However, the implant system 100 may not be limited to these enumerated elements.

The implant device 110 may generate a stimulation signal for a user through a power manager 113 according to an operation mode, based on biometric information sensed at a body 105 of the user. For example, the implant device 110 may sense a variety of biometric information from the body 105 of the user through a bio interface I/F 119. The biometric information may include, for example, a heart rate, a temperature, a blood glucose level, and a blood pressure, as non-limiting examples. However, the biometric information may not be limited to these enumerated examples. For example, the biometric information may vary depending on an application field of the implant system and/or desired usage of the implant system 100.

The implant device 110 may generate the stimulation signal for the user by supplying power to the bio I/F 119 through the power manager 113 according to an operation mode determined by one or more processors 115, based on the biometric information of the user. For example, the one or more processors 115 may determine the operation mode to be a deep sleep mode or a sleep mode, based on a power consumption according to a sleep duration of the implant device 110. In such an example, the sleep duration may correspond to a duration of a sleep time for which the implant device 110 may maintain a sleep state. The configuration of the one or more processors 115 to determine the operation mode of the implant system 100 is described below in further detail with reference to the example of FIG. 2, and an example of determining the operation mode by the one or more processors 115 is described in further detail below with reference to the example of FIG. 3.

For example, in response to the operation mode being determined to be the deep sleep mode, the one or more processors 115 may turn off an enable signal of the power management unit 113, and at the same time starting a count of a timer value, corresponding to the sleep duration. In response to the operation mode being determined to be the deep sleep mode, the one or more processors 115 may store, in a memory 117, biometric information used for each application field and/or desired usage of the implant system 100. For example, if the one or more processors 115 are woken up urgently by starting wireless charging through a wireless charger 136, the one or more processors 115 may read a final value of a real-time clock (RTC) 133. Thus, the one or more processors 115 do not need to separately store information related to the RTC 133. In such a non-limiting example, the one or more processors 115 may only need to store the biometric information or information to be used to determine a state of a patient in the memory. However, in other examples, the one or more processors 115 may store additional information in addition to or in lieu of the biometric information.

The implant device 110 may be, for example, an implantable device for an electroceutical supply for chronic treatment, or a pacemaker used to apply an artificial pulse stimulation in case of a cardiac arrest.

The wake-up device 130 may include the RTC 133 and the wireless charger 136. The wireless charger 136 may also be referred to as the "wireless power transfer device."

Hereinafter, the wireless charger and the wireless power transfer device may be interchangeably used to have the same meaning.

The wake-up device 130 may switch the operation mode based on either one or both of an energy supply through an external energy source 170, that is, a coil, different from the power manager 113, and a result of counting a timer. For example, the wake-up device 130 may turn on the enable signal of the power manager 113 for the implant device 110 to operate in an active mode, based on whether a count value of the timer of the RTC 133 has expired. Further, the wake-up device 130 may turn on the enable signal of the power manager 113, in response to receiving a wireless energy supplied through the external energy source 170. In such an example, the wake-up device 130 may turn on the enable signal of the power manager 113, in response to the wireless energy supply with respect to the wireless charger 136, irrespective of whether the count value of the timer of the RTC 133 has expired. The wake-up device 130 may turn on the enable signal of the power manager 113 based on an energy reception degree, according to the wireless energy supply. For example, if wireless energy is supplied through an external coil of the wireless charger 136 before the timer of the RTC 133 expires, charging of the wireless charger 136 may start when the supplied energy is greater than or equal to a predetermined amount of power. In such an example, an analog signal generated in response to the charging of the wireless charger 136 may be converted into a digital signal, that is, into the enable signal of the power manager 113 and then transmitted into the power manager 113.

By transmitting an operation start instruction with respect to the power manager 113 through wireless charging with respect to the wireless charger 136 to externally and urgently instruct to cause a change of mode into an active mode, the power consumption of the implant system 100 may be remarkably reduced. If the operation start instruction with respect to the power manager 113 is transmitted through wireless charging, the one or more processors 115 may switch from the power saving mode into the active mode. In case of an emergent situation in which the implant device 110 needs to urgently operate, such as due to a heart arrest of the user, a wake-up with respect to the implant device 110 may be performed by performing wireless charging with respect to the wireless charger 136, rather than waiting for a wake-up to occur due to a counting of the RTC 133.

The RTC 133 may be connected directly to a battery 150 of the implant device, and may count a timer for operation mode switching between the power saving mode and the active mode. The RTC 133 may count the timer for switching the operation mode of the implant device, for example, such as switching from the deep sleep mode to the active mode.

For example, if a mode switching event from the power saving mode to the active mode occurs, the RTC 133 or the wireless power transfer device 136 may power on the implant device 110 by turning on the enable signal of the power manager 113. The RTC 133 may turn on the enable signal of the power manager 113 in order for the implant device to operate in the active mode, based on whether a count value of the timer has expired. Further, the wireless power transfer device 136 may switch the operation mode of the implant device 110, based on whether energy is supplied by the external energy source 170 that is unrelated to the battery 150. The wireless power transfer device 136 may turn on the enable signal of the power manager 113, in response to whether wireless energy is supplied through the external energy source 170, regardless of whether the count value of the timer has expired. The wireless power transfer device 136 may turn on the enable signal of the power manager 113 based on the energy reception degree, according to the wireless energy supply.

The operation mode may include, for example, the power saving mode in which the implant device 110 is in a sleep state, and the active mode in which the implant device 110 is in an operating state. In the active mode, the implant device 110 may generate the stimulation signal and may transmit the biometric information sensed through the bio I/F 119 to the outside through using a connectivity device 192, and an antenna 190. Thus, in the power saving mode, the implant device 110 may be maintained in an idle state of not performing any operation. Accordingly, because it is maintained in such an idle state, the implant device 110 may use less power.

Further, the power saving mode may include the deep sleep mode in which the implant device 110 including the power manager 113 is in a sleep state, and the sleep mode in which the implant device 110 except for the power manager 113 is in a sleep state.

In the deep sleep mode, the implant system 100 may completely turn off the power manager 113 and the one or more processors 115 by blocking a power supply otherwise supplied with respect to the implant device 110. Thus, a power supply with respect to all the elements of the implant device 110 otherwise receiving power through the power manager 113 may also be blocked. If the operation mode is switched from the deep sleep mode to the active mode, a time required for the power manager 113 to resume the operation, that is, a "booting time," may increase, but the power consumption of the power manager 113 may decrease. If the operation mode is switched from the deep sleep mode to the active mode, the one or more processors 115 may return to the initial power-on state.

In the sleep mode, the implant system 100 may maintain the power manager 113 in an ON state, and may maintain the other elements of the implant device 110 in an OFF state. For example, a time required for the one or more processors 115 to resume its operation in response to a mode switching from the sleep mode to the active mode may be relatively short when compared to a similar time required for the deep sleep mode, but a power consumption for data retention in such an example may be relatively great.

By positioning an occurrence source of a mode switching event from the power saving mode or the deep sleep mode to the active mode outside of the power manager 113, a leakage power otherwise generated in each of the individual constituent blocks of the implant device 110 may be removed. Also, meanwhile, the overall leakage power of the implant device 110 may be minimized to only include the single leakage power consumed by the power management unit 113. The occurrence source of the mode switching event may be, for example, the wireless power transfer device 136 receiving an external charging event by the external energy source 170 and/or the RTC 133 corresponding to the timer.

The RTC 133 may operate by being connected directly to an energy supply source, for example, the battery 150, other than the power manager 113. In the deep sleep mode, by operating the RTC 133 independently of the power manager 113, the total energy consumption of the implant system 100 may be reduced accordingly.

Further, the wireless power transfer device 136 may operate when receiving external wireless energy, irrespective of the energy supply source of the external wireless energy.

For example, if the wake-up device 130 receives power from the power manager 113, the power manager 113 may continuously operate even in the deep sleep mode, and thus the individual constituent blocks of the wake-up device 130 connected to the power manager 113 may block power autonomously. In such an example, it may be difficult to control leakage power generated when the individual constituent blocks block power, and the power manager 113 may operate for the operation of the RTC 133. Thus, the voltage conversion efficiency may also decrease.

Because the wake-up device 130 does not receive power from the power manager 113, the operation of the power manager 113 may be turned off in the deep sleep mode. Thus, the generation of power used for voltage conversion and leakage power of the individual constituent blocks of the wake-up device 130 may also be removed, accordingly.

In addition to the implant device 110, the wake-up device 130 may be utilized for various systems, small in size, that wish to minimize their power consumption, for example, a wearable device, an epidermal patch system, smart dust for environmental sensing, and a home surveillance system, as non-limiting examples. However, these are only examples, and other examples not specifically enumerated may also be used in other examples.

Figure 2:
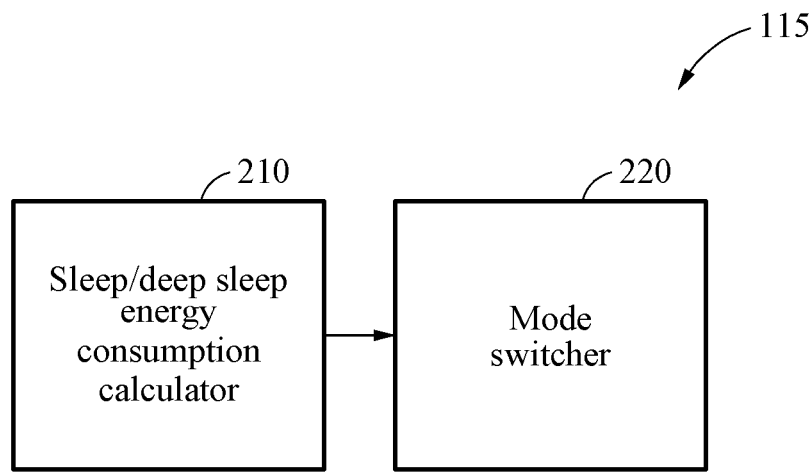
FIG. 2 illustrates an example of an operation of one or more processors.

FIG. 2 illustrates an example of an operation of one or more processors. Referring to the example of FIG. 2, the one or more processors 115 may include a sleep/deep sleep energy consumption calculator 210 and a mode switcher 220.

The one or more processors 115 may determine whether an implant device requires a sleep or an activation. For example, in response to a determination that the implant device requires a sleep, the one or more processors 115 may transition to a deep sleep mode or a sleep mode, based on a required sleep duration. For example, the one or more processors 115 may switch to the sleep mode in an example in which a standby lasting for more than a predetermined standby time for a subsequent operation is required, that is, in a situation in which a sleep mode is required. In such an example, the predetermined standby time may vary for each processor and for each application, individually. Further, the predetermined standby time may be determined based on a power consumption in a situation according to each mode, such as an active mode, a sleep mode, or a deep sleep mode. When the predetermined standby time elapses, the one or more processors 115 may switch to the sleep mode.

In response to the determination that the implant device requires a sleep, the one or more processors 115 may select a mode requiring a lower power consumption from between the deep sleep mode and the sleep mode, by using an equation described in further detail below in operation 310 of the example of FIG. 3, and may enter the selected mode.

In such an example, depending on the sleep duration, the power consumption in each of the deep sleep mode and the sleep mode may vary. Thus, the sleep/deep sleep energy consumption calculator 210 may calculate an accurate power consumption that is to be expected for each of these modes.

The sleep/deep sleep energy consumption calculator 210 may calculate the power consumption for each mode according to the sleep duration.

The mode switcher 220 may switch the operation mode of the implant system, based on the calculated power consumption for each mode.

For example, as shown below in further detail in table 600 of the example FIG. 6, in the sleep mode, the implant system may retain data and thus, may require no power consumption for a boot-up process, but may require an ongoing power consumption for an ongoing data retention.

However, in the deep sleep mode, the implant system may not have a leakage power occurring in the power manager 113, but may require additional power consumption for a boot-up process.

The sleep/deep sleep energy consumption calculator 210 may calculate an accurate power consumption for each mode according to the corresponding sleep duration, and the mode switcher 220 may optimize and switch to the operation mode of the implant system, more specifically, the power saving mode, based on the power consumption for each mode, thereby potentially reducing the energy consumption of the implant system.

Figure 3:
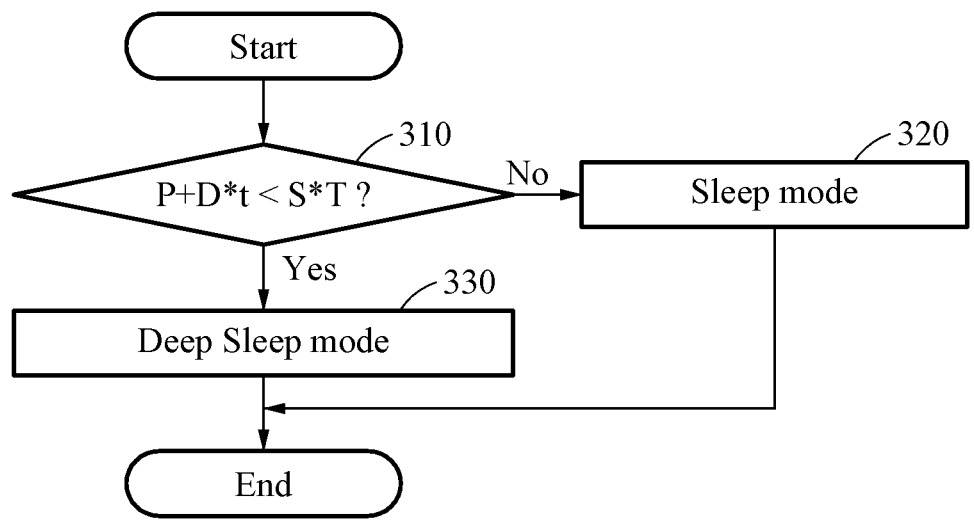
FIG. 3 is a flowchart illustrating an example of determining an operation mode by an implant device.

FIG. 3 is a flowchart illustrating an example of determining an operation mode by an implant device. Referring to the example of FIG. 3, one or more processors 115 of an implant device may determine an operation mode to be a deep sleep mode or a sleep mode, based on a result of comparing a first power consumption of an implant system operating in a deep sleep mode and a second power consumption of the implant system operating in a sleep mode, based on a sleep duration.

In operation 310, the one or more processors 115 may compare whether the first power consumption of the implant system operating in the deep sleep mode is less than the second power consumption of the implant system operating in the sleep mode. In such an example, the first power consumption may be a sum of a power consumption P for booting a power manager 113 and a power consumption D*t according to the sleep duration t in the deep sleep mode. Further, the second power consumption may be a power consumption S*t according to the sleep duration t in the sleep mode.

In response to a determination that the first power consumption is greater than or equal to the second power consumption, the one or more processors 115 may determine the operation mode to be the sleep mode, in operation 320.

In response to a determination that the first power consumption is less than the second power consumption, the one or more processors 115 may determine the operation mode to be the deep sleep mode, in operation 330.

Figure 4:
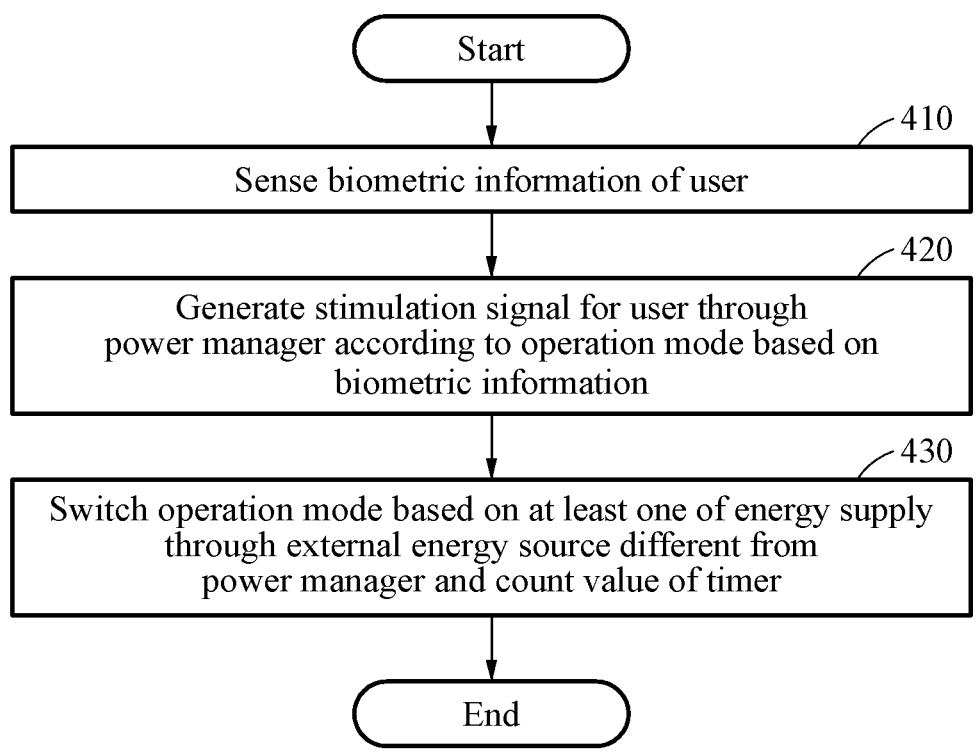
FIG. 4 is a flowchart illustrating an example of an operating method of an implant system.

FIG. 4 is a flowchart illustrating an example of an operating method of an implant system. Referring to the example of FIG. 4, in operation 410, an implant system may sense biometric information of a user.

In operation 420, the implant system may generate a stimulation signal for the user through a power manager 113 according to an operation mode, based on the sensed biometric information.

In operation 430, the implant system may switch the operation mode based on at least one of an energy supply through an external energy source, differing from the power manager 113 and a count value of a timer. For example, the implant system may counts the timer for operation mode switching between a power saving mode and an active mode. The implant system may sense at least one of whether the time has expired and whether energy is supplied by the external energy source. The implant system may switch the operation mode from the power saving mode to the active mode, in response to whether the timer has expired, or the presence of the energy supply being sensed before the timer expires.

Further, the implant system may calculate a power consumption used for booting the power manager 113 and a power consumption for each power saving mode according to the sleep duration of the implant device. The implant system may determine the operation mode to be one of the deep sleep mode or the sleep mode, based on the calculated power consumptions. The implant system may switch the operation mode to the determined mode. For example, in response to the operation mode being determined to be the deep sleep mode, the implant system may turn off an enable signal of the power manager 113, and at the same time start counting the timer based on the sleep duration. At the same time, the implant system may store, in a memory, biometric information required for each application field of the implant system.

Figure 5:
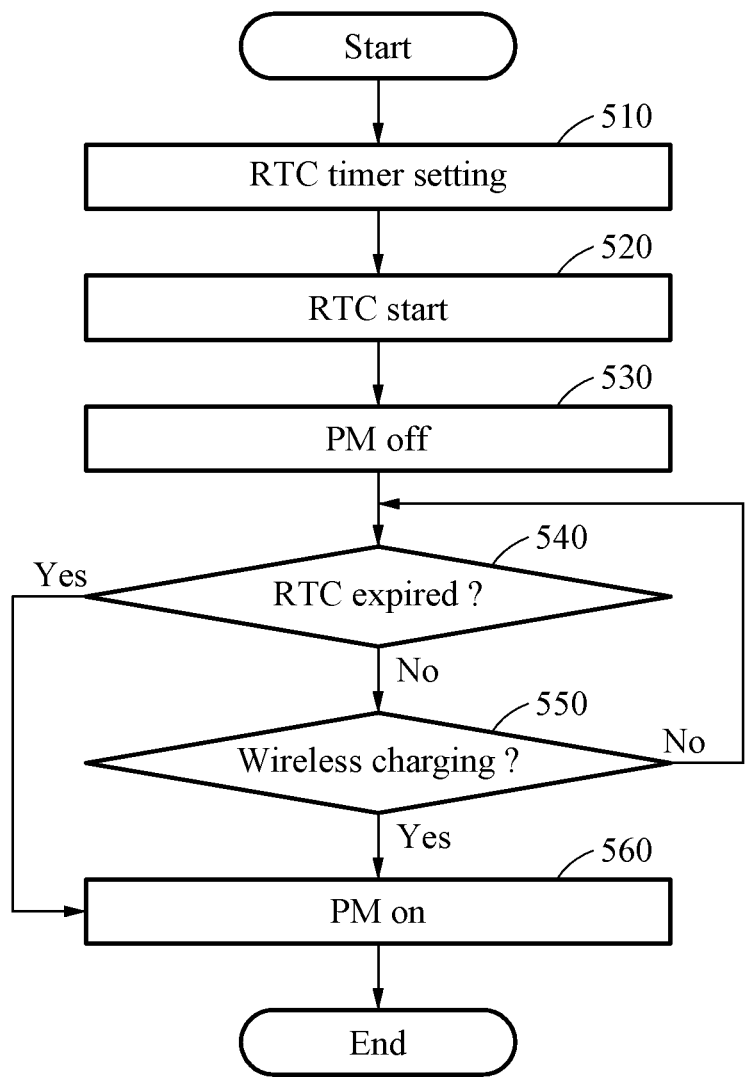
FIG. 5 is a flowchart illustrating an example of an operating method of a wake-up device.

FIG. 5 is a flowchart illustrating an example of an operating method of a wake-up device. Referring to the example of FIG. 5, in operation 510, a wake-up device may set a timer value of an RTC connected directly to a battery and configured to provide a clock, based on a sleep duration of an implant device. Then, the wake-up device may start a counting of the RTC.

In response to the RTC starting counting according to a timer value in operation 520, the wake-up device may turn off an enable signal of a power manager 113 for the implant device including the power manager 113 to operate in a power saving mode, in operation 530. When the enable signal of the power manager 113 is turned off, the implant device may operate in a deep sleep mode. In such an example, the RTC may operate using power from the battery, rather than power from the power manager 113.

In operation 540, the wake-up device may determine whether the timer value has expired. In response to the determination that the timer value has expired, the wake-up device may turn on the enable signal of the power manager 113, in operation 560.

In response to the determination that the timer value has not expired, the wake-up device may determine whether energy is supplied through an external energy source that is different from the power manager 113, in operation 550. In response to the determination that energy is not supplied through the external energy source, the wake-up device may determine whether the timer value has expired. In response to the determination that the timer value has expired, the wake-up device may turn on the enable signal of the power manager 113, in operation 560.

In response to the determination that energy is being supplied through the external energy source, the wake-up device may turn on the enable signal of the power manager 113.

Figure 6:
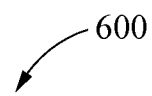
FIG. 6 illustrates an example of a result of comparing a power consumption in a sleep mode and a power consumption in a deep sleep mode.

FIG. 6 illustrates an example of a result of comparing a power consumption in a sleep mode and a power consumption in a deep sleep mode. Referring to the example of FIG. 6, table 600 shows a result of comparing respective items in a sleep mode and a deep sleep mode.

In the sleep mode, a power consumption for data retention, leakage power of an individual block of the implant device, also referred to as the "individual block leakage," a power consumption according to voltage conversion of the power manager 113, also referred to as the "PM conversion energy,", and a leakage power of the power manager 113, also referred to as the "PM leakage," may occur. Further, in the sleep mode, a battery power consumption for driving an RTC may occur, but a power consumption for booting up one or more processors 115 and/or the power manager 113 does not occur.

However, in the deep sleep mode, a power consumption for data retention, leakage power of the individual block of the implant device, also referred to as the "individual block leakage," a power consumption according to voltage conversion of the power manager 113, also referred to as the "PM conversion energy," and leakage power of the power manager 113 the "PM leakage" do not occur. Further, in the deep sleep mode, a battery power consumption used for driving the RTC and a power consumption for booting up the one or more processors 115 and/or the power manager 113 occurs.

According to one or more examples, an implant system may calculate an accurate power consumption expected for each power saving mode based on a sleep duration, then selectively operating the power saving mode as a deep sleep mode or a sleep mode according to a calculated sleep duration, thereby reducing the energy consumption of the implant system as a result.

The implant system, implant device, wake-up device, implant system 100, implant device 110, power manager 113, one or more processors 115, memory 117, bio I/F 119, wake-up device 130, RTC 133, wireless charger 136, connectivity device 192, sleep/deep sleep energy consumption calculator 210, mode switcher 220, and other apparatuses, units, modules, devices, and other components described herein with respect to FIGS. 1-6 are implemented by hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-6 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. The instructions or software may be written using any programming language based on the block diagrams and the flow charts illustrated in the drawings and the corresponding descriptions in the specification, which disclose algorithms for performing the operations performed by the hardware components and the methods as described above.

The instructions or software to control computing hardware, for example one or more processors or computers, to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A system comprising:
   an implantable device comprising a battery, and a power manager, wherein the implantable device operates according to an operation mode, wherein the operation mode includes a power saving mode in which the implantable device is in a sleep state and an active mode in which the implantable device is in an operating state; and
   a wake-up device comprising:
      a real-time clock (RTC) connected directly to the implantable device and configured to count a time value for switching the operation mode between the power saving mode and the active mode; and
      a wireless power transfer device configured to sense whether a wireless power is wirelessly supplied from an external power source separate from the battery, switch the operation mode as the wireless power is wirelessly supplied from the external power source, and turn on an enable signal of the power manager to operate in the active mode based on a result of the sensing, irrespective of whether a count value of the time value has expired.

2. The wake-up device of claim 1, wherein the wireless power transfer device is configured to turn on the enable signal of the power manager when the power wirelessly supplied is greater than or equal to a predetermined amount of power.

3. An operating method of a wake-up device, the operating method comprising:
   determining a sleep duration for which an implantable device maintains a sleep state;
   setting a time value of a real-time clock (RTC) based on the sleep duration, wherein the RTC is connected directly to a battery and is configured to provide a clock and count according to the time value; and
   switching an operation mode of the implantable device between a power saving mode in which the implantable device is in the sleep state and an active mode in which the implantable device is in an operating state, in response to whether a wireless power is wirelessly supplied through an external wireless charger different from the battery, including:

sensing the RTC starting a counting according to the time value, wherein the implantable device includes the power manager and turning off an enable signal of the power manager for the implantable device to operate in the power saving mode, based on the sensing the RTC starting a counting according to the time value, wherein the implantable device includes the power manager; and sensing the wireless power is wirelessly supplied through the external wireless charger different from the battery and turning on the enable signal of the power manager for the implantable device to be activated and operate in the active mode based on a result of the sensing the wireless power is wirelessly supplied through the external wireless charger different from the battery, irrespective of whether the time value of the RTC has expired.

\* \* \* \* \*